Figure 1:
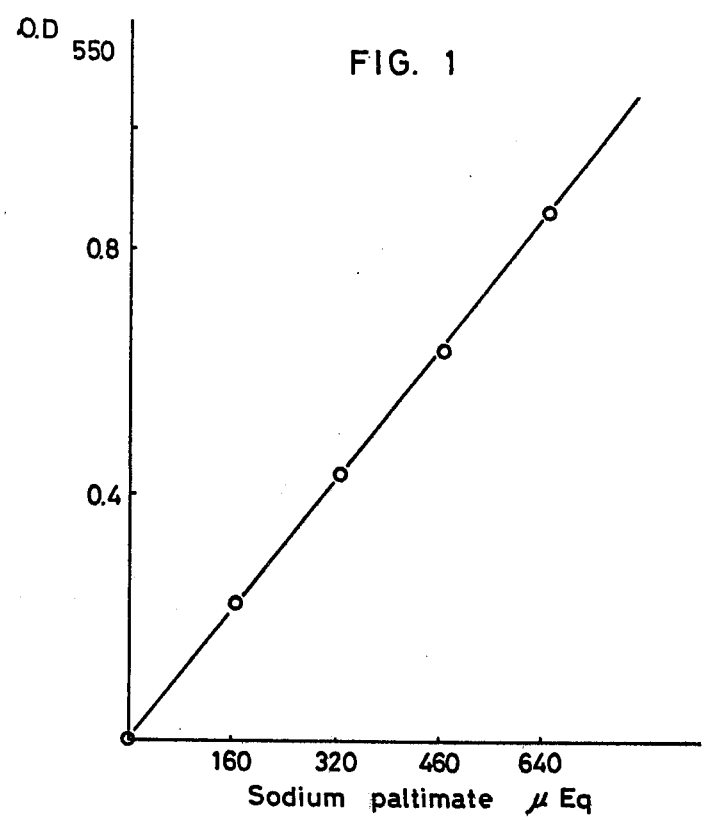

United States Patent [19]

Kikuchi et al.

[11] 4,301,244
[45] Nov. 17, 1981

[54] QUANTITATIVE ANALYSIS OF FREE FATTY ACID AND REAGENT COMPOSITION THEREFOR

[75] Inventors: Toshiro Kikuchi; Makoto Ando, both of Tsuruga, Japan

[73] Assignee: Toyo Boseki Kabushiki Kaisha, Japan

[21] Appl. No.: 121,166

[22] Filed: Feb. 13, 1980

[30] Foreign Application Priority Data

Feb. 13, 1979 [JP] Japan .................................. 54-15696

[51] Int. Cl.³ .......................... C12Q 1/00; C12Q 1/26
[52] U.S. Cl. ........................................ 435/4; 435/25; 435/27; 435/28; 435/189; 435/810; 435/923; 435/924
[58] Field of Search ..................... 435/4, 25, 183, 189, 435/27, 28, 921, 923, 924, 810

[56] References Cited

U.S. PATENT DOCUMENTS

| | | | |
|---|---|---|---|
| 3,979,262 | 9/1976 | Hunziker | 435/28 |
| 4,071,413 | 1/1978 | Takahashi et al. | 435/4 |
| 4,101,381 | 7/1978 | Klose et al. | 435/27 |
| 4,229,538 | 10/1980 | Yamada et al. | 435/15 |

OTHER PUBLICATIONS

Chemical Abstracts, 89:159269d, "Acyl–CoA Oxidase of Rat Liver", p. 220, 1978.
Chemical Abstracts, 85:188245r, A Soluble-Coenzyme A Oxidase from the Yeast *Candida utilis*, 1976.
Chemical Abstracts, 90:135464h, Subcellular Distribution of the Enzymes of Fatty Acyl-CoA B-Oxidation System, 1979.
Takahashi et al. "Rinsho Kagaku", 4, 1975, pp. 179–185.

Primary Examiner—Peter A. Hruskoci
Attorney, Agent, or Firm—Wenderoth, Lind & Ponack

[57] ABSTRACT

There is provided a method for the quantitative analysis of a free fatty acid which comprises (1) the first step of treating a sample containing the free fatty acid with acyl-coenzyme A synthetase in the presence of adenosine triphosphate and coenzyme A to form acyl-coenzyme A, (2) the second step of oxidizing said acyl-coenzyme A, in the presence of oxygen, with acyl-coenzyme A oxidase produced by a microorganism of the genus Candida to form enoyl-coenzyme A and hydrogen peroxide, and (3) the third step of (a) measuring the amount of the formed enoyl-coenzyme A or hydrogen peroxide or (b) measuring the amount of oxygen consumed in said oxidation reaction, to thereby determine the amount of free fatty acid in said sample.

8 Claims, 2 Drawing Figures

QUANTITATIVE ANALYSIS OF FREE FATTY ACID AND REAGENT COMPOSITION THEREFOR

The present invention relates to a quantitative analysis of free fatty acid using both acyl-coenzyme A synthetase (hereinafter referred to acyl-CoA synthetase) and acyl-coenzyme A oxidase produced by microorganism (hereinafter referred to acyl-CoA oxidase produced by microorganism), and reagent composition therefor. More particularly, the invention concerns a quantitative analysis of free fatty acid comprising causing acyl-CoA synthetase and acyl-CoA oxidase produced by microorganism to act on free fatty acid in a sample in the presence of oxygen material and measuring the amount of hydrogen peroxide or enoylcoenzyme A (hereinafter referred to enoyl-CoA) thus produced or the amount of oxygen consumed in the oxidation reaction, and reagent composition therefor.

Heretofore, as a quantitative analysis of free fatty acid in serum, various methods have been proposed as, for example, a method wherein the free fatty acid extracted by a fat-soluble organic solvent is measured by a neutralization titration with an alkali, and a method wherein the free fatty acid is treated with copper nitrate and triethanolamine to give copper salt of said free fatty acid, which is extracted with chloroform and then reacted with a chelating agent to develop color. However, in the former method, there is a problem of relatively poor reproducibility because of the complicated operations with organic solvent, adverse effect of the presence of organic acids, technical error inevitable in the titration operation and the like, and in the latter method, there are problems of complicated operations in the formation of copper salts, with organic solvent, and of possible harmful effect on human body and the like. Therefore, in clinical examination, they are too complicated to standardize the operational details.

Very recently, has been produced a novel method, by Takahashi et al, which comprises making acyl-CoA synthetase act on free fatty acid and measuring thus formed adenosine monophosphate (hereinafter referred to AMP) by the use of the myokinase, pyruvate kinase system ("Rinsho Kagaku" 4, 179, 1975). However, this method requires unstable, expensive reagents as reduced nicotinamide adenine dinucleotide (hereinafter abreviated as NADH), and phosphoenolpyruvic acid, and four kinds of enzymes, which involves technical difficulties, and therefore, this has not been practically used up to the present day.

Under the circumstances, the inventors, have searched for a more practical method being free of the above-mentioned drawbacks, have arrived at the present invention. That is, the invention offers a method for quantitative analysis of free fatty acid which is characterized by causing acyl-CoA synthetase to act on the free fatty acid in the presence of adenosine triphosphate (hereinafter abbreviated as ATP) and coenzyme A (hereinafter referred to CoA), reacting the thus formed acyl-CoA, in the presence of oxygen, with acyl-CoA oxidase produced by microorganism, and measuring the amount of hydrogen peroxide or enoyl-CoA thus formed or the amount of oxygen consumed in said oxidation reaction. The invention also provides a reagent composition for use in the determination of free fatty acid, comprising acyl-CoA synthetase, acyl-CoA oxidase produced by microorganism, CoA and ATP.

The series of enzymatic reactions may be shown as follows:

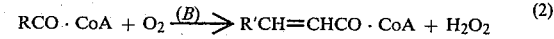

wherein (A) is acyl-CoA synthetase, (B) is acyl-CoA oxidase produced by microorganism, RCOOH is free fatty acid (in which R represents a long-chain alkyl having 5 to 22 carbon atoms), ATP is adenosine triphosphate, CoA is coenzyme A, RCO.CoA is acyl-CoA, AMP is adenosine monophosphate, PPi is pyrophosphoric acid and R'CH=CHCO.CoA is enoyl-CoA (in which R' is the same alkyl as stated in said R, excepting excluding $-CH_2CH_2-$).

The acyl-CoA synthetase as used in the present invention is acid:CoA ligase (AMP), which is also known as fatty acid thiokinase (long chain), whose enzyme code number is (E.C 6,2,1,3). This enzyme is found in animal organs such as rat liver, chicken liver and the like, and also in various microorganisms belonging to, for example, *Escherichia coli*, genus Pseudomonas, genus Bacillus, genus Candida, genus Nocardia and the like. This plays a part in the first step in the fatty acid β-oxidation system of converting free fatty acid with 5 to 22 carbon atoms and especially 12 to 18 carbon atoms, to acyl-CoA. An optimum pH is said to be around 7.5 to 9.0 and Km (Michaelis constant) is less than $10^{-4}$ M.

The acyl-CoA oxidase produced by microorganism as used in the present invention is a kind of enzyme, which, when acting acyl-CoA in the presence of oxygen, can produce enoyl-CoA and hydrogen peroxide. Highly purified acyl-CoA oxidase has only been obtained from rat liver (Proceedings of Japanese Conference on the Biochemistry of Lipids vol. 20, 1978).

However, the present inventors have succeeded in obtaining highly purified acyl-CoA oxidase from microorganisms, and especially from yeast belonging to Genus Candida. This enzyme has been reported in detail in our co-pending Japanese Patent Application No. 24232/1979. Briefly stated, this enzyme is characterized in that (1) when acting on acyl-CoA in the presence of oxygen, this causes the formation of enoyl-CoA and hydrogen peroxide, (2) the substrate for this enzyme is acyl-CoA whose acyl moiety has 6 to 22 carbon atoms, and (3) optimum pH is 6.5 to 9.0, although the stabilizing pH is 7.0 to 8.5. This enzyme can be obtained by the process comprising cultivating an acyl-CoA oxidase-producing microorganism belonging to the genus Candida e.g. *Candida tropicalis* IFO 0589 (ATCC 20115) and *Candida lipolytica* IFO 1548 (ATCC 18942) in a nutrient medium, thereby accumulating acyl-CoA oxidase in yeast cells, and separating the acyl-CoA oxidase from said cells.

According to the present invention, in the first step thereof, free fatty acid with 5 to 22 carbon atoms is treated with acyl-CoA synthetase in the presence of ATP and CoA, and preferably in the presence of magnesium ions, to form acyl-CoA, AMP and pyrophosphoric acid. The acyl-CoA synthetase is preferably a highly purified preparation. The reaction is preferably carried out at a temperature of 20° to 40° C. and at a pH ranging from 6 to 9.5. In this reaction system, dithiothreitol, mercaptoethanol, glutathione (reduced form) or the like may be present as an antioxidant.

In the next reaction step, the thus formed acyl-CoA is treated with acyl-CoA oxidase produced by mocroorganism, in the presence of oxygen, to give enoyl-CoA and hydrogen peroxide. The acyl-CoA oxidase produced by microorganism is preferably of genus Candida and especially of *Candida lipolytica,* and in highly purified form. The reaction conditions may preferably be selected at a temperature of 20° to 40° C. and a pH of 6 to 9.5 FAD (flavin adenin dinucleotide) may also be present in this reaction system. The abovesaid first and second reactions may be carried out in one step or two separate steps, and thus formed hydrogen peroxide or enoyl-CoA is determined according to a conventional quantitative analysis method.

As the quantitative analysis of hydrogen peroxide, the following methods [A] and [B] are known.

[A] The hydrogen peroxide generated by the action of acyl-CoA oxidase produced by microorganism is converted, according to the reaction formula (3) undermentioned, through the reaction with alcohol in the presence of catalase, to an aldehyde, which is measured for the determination of free fatty acid.

(3)

In this measurement, two methods are of significance, one being the method wherein the aldehyde is directly subjected to a colorimetry and the other being the method wherein the aldehyde is conjugated with a dehydrogenase system and the change in absorption in the ultraviolet region of NAD(NADH) is determined. In general, a catalase system is scarcely affected by reducing substances. Therefore, the effect of such a reducing substance as CoA included in the present reaction mixture may be negligible, which is a prominent advantage of the present method. As the colorimetric method, the following methods are known.

(a) The produced formaldehyde is condensed with acetylacetone and ammonia and the developed yellow color (of diacetyl dihydrolutidine) is compared at 412 nm with that of a standard.

(b) The formed aldehyde is condensed with 2 molecules of 3-methyl-2-benzothiazolinone hydrazone (hereinafter abreviated as MBTH) in the presence of oxidizing agent, and the developed blue color is compared at 620 nm with that of a standard.

(c) The formed formaldehyde is condensed with 4-amino-3-hydrazino-5-mercapto-1,2,4-triazole, and the developed purple color is compared at 550 nm with that of a standard.

These are, however, given just for illustration purpose and any method capable of determining the aldehyde produced by the action of catalase on hydrogen peroxide-alcohol system may successfully be used in the present invention.

As the ultraviolet method, the following may be mentioned.

(a) The aldehyde produced by the action of catalase and alcohol is reacted in the presence of NADH with alcohol dehydrogenase and the decrease in absorbance of NADH at 340 nm is measured.

(b) The aldehyde is reacted, in the presence of NAD, with aldehyde dehydrogenase, and the increase at 340 nm due to the formation of NADH is measured.

However, any method in this category and capable of determining the formed aldehyde may likewise be used in the present invention.

[B] Hydrogen peroxide generated by the action of acyl-CoA oxidase produced by microorganism is reacted, in the presence of peroxidase, with a hydrogen donor (chromogen) which will develop color (fluorescence) when oxidized and the formed color-developed substance (fluorescent substance) is measured for the determination of free fatty acid.

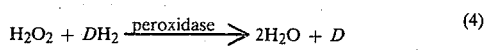
(4)

wherein D represents hydrogen donor.

In this method, the effect of reducing substance present in the reaction mixture or the sample material cannot be neglected and therefore, in order to obtain a precise quantitative relationship with the amount of free fatty acid, the employment of fixed conditions are required.

As the colorimetric method, the following may be used.

(a) 4-Aminoantipyrin (hereinafter abreviated as 4-AA) and phenol are used as chromogens and the color comparison is made at 505 nm (red color).

(b) 3-Methyl-2-benzothiazolinone hydrazone (hereinafter abreviated as MBTH) and dimethylaniline (hereinafter abreviated as DMA) are used as chromogens and the color comparison is made at 590 nm (blue color).

(c) 4-AA and DMA or diethylaniline (hereinafter abreviated as DEA) are used as chromogens and the color comparison is made at 550 nm (pure color).

However, in the present invention, any colorimetric method other than the abovesaid three may be used, by providing such hydrogen donor (chromogen) for imparting color by the action of oxidizing agent of hydrogen peroxide in the presence of peroxidase. It is also possible to measure the amount of hydrogen peroxide generated by the action of acyl-CoA oxidase, by using an electrode of hydrogen peroxide.

In carrying out the above-mentioned methods, the measurement of hydrogen peroxide may be done simultaneously with the abovesaid first and second reactions. In such a measurement of hydrogen peroxide with chromogen and peroxidase for the determination of free fatty acid, when an excessive quantity of CoA is added to the reaction system, the desired sensitivity cannot be obtained because of the obstructed color development under the influence of said reducing substance.

As a method for determining enoyl-CoA, mention is made of the process in which an enzymatic system comprising enoyl-CoA hydratase, 3-hydroxyacyl-CoA dehydrogenase and nicotinamide adenine dinucleotide (NAD) engage in a coupling reaction and the amount of thus produced reduced form nicotinamide adenine dinucleotide (hereinafter abreviated as NADH) is measured by the increase at $OD_{340}$.

Measurement of oxygen consumption in the oxidation reaction may be carried out in a conventional way. For example, this may be electrically determined by polarimetry.

According to the present invention, free fatty acid can be easily determined by making use of two and more than two enzymes. In contrast to heretofore known methods, measurement is directly made of hydrogen peroxide derived from acyl-CoA produced by free fatty acid. Therefore, there are only small enzymatic errors and the reproducibility of the process is excellent. This method is further characterized in its operational ease in carrying out the above-mentioned colorimetry or measurement in the ultraviolet region.

When an acyl-CoA oxidase of rat liver origin is to be used, there is a problem of poor reactivity and the reaction proceeds with only 60% of the free fatty acid. However, in the case of the present acyl-CoA oxidase produced by microorganism, the reaction will proceed with almost 100% of free fatty acid because of excellent reactivity thereof.

In the employment of microbodies of yeasts belonging to genus Candida, there are problems such that preparation of said microbody is very difficult and thus obtained microbody is quite unstable and of poor activity and therefore it cannot be a commercial product. Furthermore, the microbody may give various side-reactions as, for example, direct reaction between hydrogen peroxide and catalase in the microbody, and therefore, it is difficult to carry out precise determination of free fatty acid.

On the other hand, in the present invention, separated and highly purified acyl-CoA oxidase produced by microorganism is used and hence, no such side-reactions are involved and an almost complete free fatty acid determination can be realized.

Figure 2:
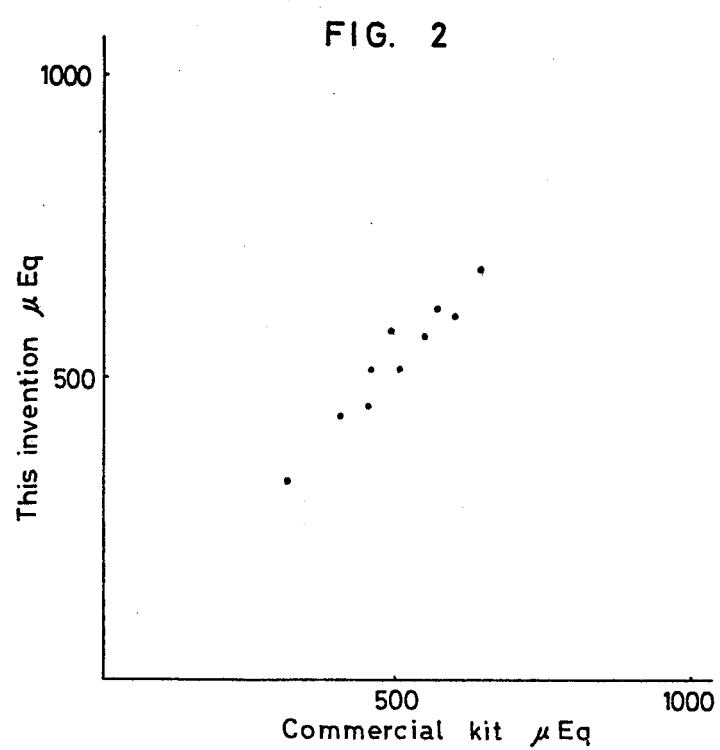

The invention shall be now more fully explained in the following Examples, which will be made by referring partly to the accompanying drawings wherein FIG. 1 is a calibration curve with palmitic acid and FIG. 2 is a graph showing the results obtained by the method of this invention as compared with those obtained by a commercial kit.

The enzymes used in these examples are as follows:
Acyl-CoA synthetase:

Candida lypolytica is cultivated in a glucose medium and the cells are collected and disrupted by means of glass beads. The supernatant is separated and repeatedly purified by using DEAE-cellulose, Sephadex G-150 and the like. Acyl-CoA oxidase:

Candida lypolytica is cultivated in an oleic acid medium and the cells are collected and disrupted by means of glass beads. The supernatant is separated, heat-treated and then repeatedly purified by using DEAE-cellulose, Sephadex G-150 and the like.

EXAMPLE 1

The under-mentioned reagent composition was prepared for the determination of free fatty acid.
Reaction mixture:

| 50 mM | potassium phosphate buffer (pH 7.8) | |
| 5 mM | EDTA . 3Na | |
| 4% | methanol | |
| | catalase | 800 U/ml |
| 10 mM | FAD (flavin adeninedinucleotide) | |
| 1 mM | CoA | |
| 10 mM | ATP | |
| 5 mM | MgCl$_2$ | |
| | acyl-CoA synthetase | 0.5 U/ml |
| | acyl-CoA oxidase | 0.5 U/ml |
| Color forming solution A | 2N KOH | |
| Color forming solution B | 0.6% AHMT(0.5N HCl) | |
| Color forming solution C | 0.75% NaIO$_4$ (0.2N KOH) | |

50 μl of sodium palmitate solution (1% Triton X-100 solution) were pipetted into a tube and 0.5 ml of the reaction mixture was added thereto. After reacting at 37° C. for 15 minutes, 0.5 ml of color forming solution A was added to the mixture and the reaction was stopped at this stage. After adding 0.5 ml of color forming solution B, the mixture was kept standing for 5 minutes and then color forming solution C was added and stirred well. After standing for an additional 10 minutes, the absorbance was measured at OD$_{550}$, using water as reference solution. For a blank test, CoA was added after the addition of color forming solution A. The calibration curve is as shown in FIG. 1.

EXAMPLE 2

Using the same reagent composition as stated in Example 1, 10 samples of serum were analyzed in regard to free fatty acid content thereof. The correlation between the measurements and the corresponding values obtained by using commercial kit (chemical method) is shown in FIG. 2, wherein y=1.049 X+17.27, r=0.959 (coefficient of correlation). In the latter measurement, to a 50 μl sample material was added 3.0 ml of extraction medium (chloroform solution) and 1.0 ml of copper solution, and the mixture was shaken for 2 minutes and then centrifugated for 5 minutes at 3000 r.p.m. 2.0 ml of the supernatant was added with 0.5 ml of color forming solution and the absorbance at 610 nm was measured. The calibration curve and the calculation method used are as usual.

COMPARATIVE EXAMPLE 1

Using the acyl-CoA oxidase (ACO) of rat liver in place of the present oxidase (ACO) produced by microorganism, the free fatty acid determination was carried out. In this experiment, 50 μl of sodium palmitate solution (1% Triton X-100 1000 μEq./1) were added with 0.5 ml of the understated reaction mixture and the similar procedures as stated in Example 1 were repeated. That is, the same coloring solutions were added to develop color and the amounts of sodium palmitate was measured.

Reaction mixture:

| 50 mM | potassium phosphate buffer (pH 7.8) | |
| 5 mM | EDTA . 3Na | |
| 4% | methanol | |
| | catalase | 800 U/ml |
| 10 mM | FAD | |
| 1 mM | CoA | |
| 10 mM | ATP | |
| 5 mM | MgCl$_2$ | |
| | Acyl-CoA synthetase rat liver derived | 0.5 U/ml |
| | Acyl-CoA oxidase | 0.5 U/ml |

TABLE 1

| minutes | Rat liver ACO Sodium palmitate (μEq./l) | microorganism ACO Sodium palmitate (μEq./l) |
| --- | --- | --- |
| 0 | 0 | 0 |
| 5 | 270 | 850 |
| 10 | 497 | 985 |
| 15 | 586 | 1005 |
| 20 | 623 | 1020 |
| 30 | 630 | 1015 |

When rat liver acyl-CoA oxidase is used in the determination of fatty acid, the reaction does not proceed in full and stops at the stage of about 60% reaction. However, in case of acyl-CoA oxidase produced by microorganism, the reaction can proceed almost 100% and therefore, this is quite suitable for the quantitative analysis of free fatty acid.

COMPARATIVE EXAMPLE 2

Microbodies were prepared from the yeast belonging to genus Candida, as follows. *Candida tropicalis* strain IFO 0589 (ATCC 20115) was inoculated to 50 ml of a medium containing 1.0% n-alkane mixture ($C_{10}$–$C_{13}$), 0.5% $KH_2PO_4$, 0.5% $K_2HPO_4$, 0.7% yeast extract and 0.7% polypeptone (pH 5.5), and cultivated, in Sakaguchi flask, with shaking for 16 hours in 30° C. Thus obtained seed culture was inoculated in each 10 flasks of medium (each 2 liter flask containing 500 ml of the above-mentioned culture medium) and cultivated with shaking for an additional 16 hours. The cultured mediums were filtered to collect 80 g (in wet) of cells, which were thoroughly washed with 50 mM potassium phosphate buffer (pH 7.5) and then suspended in 400 ml of the same buffer. The suspension was treated with zymolyase to form protoplast, which was disrupted by means of a homogenizer and then subjected to centrifugation (3000 g) for 15 minutes. The supernatant was further centrifuged (20000 g) for 1 hour to obtain the precipitation, which was used in the subsequent tests as microbody fraction.

Comparative tests were carried out with the above-mentioned microbodies and with the present oxidase (ACO) produced by microorganism in the determination of free fatty acid. That is, 50 μl of sodium palmitate solution (1% Triton X-100) were added with 0.5 ml of the following reaction mixture and the mixture was reacted at 37° C. as in Example 1.

Reaction mixture:

| | | |
|---|---|---|
| 50 mM | potassium phosphate buffer (pH 7.8) | |
| 5 mM | EDTA . 3Na | |
| 4% | methanol | |
| | catalase | 800 U/ml |
| 10 mM | FAD | |
| 1 mM | CoA | |
| 10 mM | ATP | |
| 5 mM | $MgCl_2$ | |
| | Acyl-CoA synthetase | 0.5 U/ml |
| | microbodies | 1 mg protein/ml |

For the comparison, experiment of Example 1 was repeated at the same time. After the reaction, the mixture was added with the color forming solutions to develop color as in Example 1 and the reactivity was examined. The results are shown in Table 2.

TABLE 2

| reaction time (minutes) | microbodies Sodium palmitate (μEq./l) | microorganism ACO Sodium palmitate (μEq./l) |
|---|---|---|
| 0 | 0 | 0 |
| 5 | 387 | 850 |
| 10 | 440 | 985 |
| 15 | 423 | 1005 |
| 20 | 480 | 1020 |
| 30 | 505 | 1015 |

When the above-mentioned microbodies were used, the recovery of hydrogen peroxide from palmitic acid was very poor. Therefore, this may not be used in practice for the determination of free fatty acid in serum.

What we claim is:

1. A method for the quantitative analysis of a free fatty acid which comprises (1) the first step of treating a sample containing the free fatty acid with acyl-coenzyme A synthetase in the presence of adenosine triphosphate and coenzyme A to form acyl-coenzyme A, (2) the second step of oxidizing said acyl-coenzyme A, in the presence of oxygen, with acyl-coenzyme A oxidase produced by a microorganism of the genus Candida to form enoyl-coenzyme A and hydrogen peroxide, and (3) the third step of (a) measuring the amount of the formed enoyl-coenzyme A or hydrogen peroxide or (b) measuring the amount of oxygen consumed in said oxidation reaction, to thereby determine the amount of free fatty acid in said sample.

2. The method as claimed in claim 1 wherein the first step is conducted at a temperature of 20° to 40° C. and at a pH of from 6 to 9.5.

3. The method as claimed in claim 1 wherein the second step is conducted at a temperature of 20° to 40° C. and at a pH of from 6 to 9.5

4. The method as claimed in claim 1 wherein the first step and second step are conducted simultaneously.

5. The method as claimed in claim 1 wherein the first step, second step and third step are conducted simultaneously.

6. The method as claimed in any of claims 1 to 5 wherein the microorganism is selected from the group consisting of *Candida lipolytica* and *Candida tropicalis*.

7. A reagent kit for the determination of free fatty acid which comprises acyl-coenzyme A synthetase, acyl-coenzyme A oxidase produced by a microorganism of the genus Candida, coenzyme A and adenosine triphosphate.

8. The kit as claimed in claim 7 wherein said microorganism is *Candida lipolytica* or *Candida tropicalis*.

* * * * *